(12) United States Patent
Halevy-Politch et al.

(10) Patent No.: US 8,402,829 B2
(45) Date of Patent: *Mar. 26, 2013

(54) INTERACTIVE ULTRASOUND-BASED DEPTH MEASUREMENT FOR MEDICAL APPLICATIONS

(75) Inventors: Jacob Halevy-Politch, Haifa (IL); Andre Craft, Haifa (IL)

(73) Assignee: Jet-Guide Ltd., Misgav (IL)

( * ) Notice: Subject to any disclaimer, the term of this patent is extended or adjusted under 35 U.S.C. 154(b) by 257 days.

This patent is subject to a terminal disclaimer.

(21) Appl. No.: 12/789,041

(22) Filed: May 27, 2010

(65) Prior Publication Data

US 2010/0240002 A1 Sep. 23, 2010

Related U.S. Application Data

(63) Continuation of application No. 11/794,620, filed as application No. PCT/IL2005/001210 on Nov. 16, 2005, now Pat. No. 7,748,273.

(30) Foreign Application Priority Data

Jan. 3, 2005 (IL) .......................... 166115

(51) Int. Cl.
*G01N 29/00* (2006.01)
*A61B 8/00* (2006.01)
*A61B 17/32* (2006.01)

(52) U.S. Cl. .............. 73/627; 73/598; 73/600; 600/437; 606/79

(58) Field of Classification Search ............ 73/597–600, 73/602, 627, 630; 606/53, 79–80, 169–172; 600/437, 443–447, 459, 471, 562–564
See application file for complete search history.

(56) References Cited

U.S. PATENT DOCUMENTS

| 4,012,842 | A | * | 3/1977 | Vit ................................. 433/216 |
| 4,375,818 | A | * | 3/1983 | Suwaki et al. ................ 600/463 |
| 4,966,152 | A | * | 10/1990 | Gang et al. .................... 600/453 |
| 5,006,984 | A | * | 4/1991 | Steele ........................... 600/587 |
| 5,013,241 | A | * | 5/1991 | von Gutfeld et al. .......... 433/86 |
| 5,115,813 | A | * | 5/1992 | Ylander et al. ............... 600/437 |
| 5,235,981 | A | * | 8/1993 | Hascoet et al. ............... 600/437 |
| 5,394,875 | A | * | 3/1995 | Lewis et al. .................... 600/445 |
| 5,402,781 | A | * | 4/1995 | Dimarogonas ............... 600/407 |
| 5,483,965 | A | * | 1/1996 | Wiener et al. ................. 600/449 |

(Continued)

FOREIGN PATENT DOCUMENTS

| JP | 3501930 | 5/1991 |
| JP | 9503932 | 4/1997 |

(Continued)

OTHER PUBLICATIONS

Office Action for EP1836487 dated Sep. 30, 2010.

(Continued)

*Primary Examiner* — Helen C. Kwok
(74) *Attorney, Agent, or Firm* — Dvorah Graeser; Graeser Associates International Inc

(57) ABSTRACT

A device for determining the internal structure of a bone along a path directed into the bone (or other tissue) is disclosed. The device comprises a nozzle fluidically connected to a liquid reservoir for providing a liquid jet directed at the bone in the direction of the path; an ultrasonic transducer for generating ultrasonic waves through the liquid jet and for detecting echoes of the ultrasonic waves caused by changes in the acoustical impedance in the bone characterizing changes in the structure of the bone along the path; and an analyzer for interpreting the echoes into meaningful information relating to the location of the structural changes along the path.

16 Claims, 7 Drawing Sheets

U.S. PATENT DOCUMENTS 5,518,008 A * 5/1996 Cucchiaro et al. ............ 600/590
5,564,423 A * 10/1996 Mele et al. .................... 600/438
7,748,273 B2 * 7/2010 Halevy-Politch et al. ...... 73/627

FOREIGN PATENT DOCUMENTS

| JP | 2001204735 | 7/2001 |
| JP | 2003503099 | 1/2003 |
| JP | 2004008432 | 1/2004 |
| JP | 2004041516 | 2/2004 |

OTHER PUBLICATIONS

Office Action for JP2007-548955 dated Aug. 3, 2010.

* cited by examiner

INTERACTIVE ULTRASOUND-BASED DEPTH MEASUREMENT FOR MEDICAL APPLICATIONS

This application is a Continuation application of, and claims priority from, U.S. patent application Ser. No. 11/794,620, filed on 3 Jul. 2007, now U.S. Pat. No. 7,748,273 which claims priority from PCT Application No PCT/IL2005/001210, filed on 16 Nov. 2005, which claims priority from Israeli Application No. IL166115, filed on 3 Jan. 2005, all of which are hereby incorporated by reference as if fully set forth herein.

FIELD OF THE INVENTION

The present invention relates to a method and device for improved depth measurement during surgery. More specifically it provides a medical tool that either includes a liquid jet or to which a liquid jet can be added, and an ultrasound wave generator that transmits ultrasound waves and detects echoes through this jet of liquid, for determining the internal structure within the bone along a path in front of the tool, and measuring locations of structural changes along that path.

BACKGROUND OF THE INVENTION

The present invention is hereinafter explained with reference to dental surgery. However the applications of the present invention are not limited to dental surgery only, and in fact include any surgery involving the use of a medical tool, which is intended to penetrate into tissue and bone such as in orthopedics, general surgery and other such fields.

For planning an implantation procedure, which is performed by an oral and maxillofacial surgeon, in the mandible or the maxilla, the patient undergoes an x-ray imaging, computer tomography (CT) and a panoramic imaging. From these images, the surgeon is able to plan the implantation procedure and also to take-out the data about the mandible, such as the depth of the canal that contains the nerve and the thickness of this bone. These imaging methods do not provide the surgeon with required information in real time, concerned with the distance between the bottom part of the drill and the top part of the canal that contains the nerve.

The present invention completes the information obtained by the CT and the panoramic imaging, by guiding the surgeon during the drilling process thus enhancing prevention of injuries during the surgery. It provides a method and device for measuring the distance between the bottom part of a dental drill and vulnerable parts (such as the canal that contains the nerve in the lower mandible) in a patient's bone during an implantation surgery process. For example, the invention can be integrated into a dental drill to provide the dental surgeon with real time guiding location of the drill tip in the patient's bone during implantation surgery.

With the present invention the surgeon can know where the drill tip is relative to sensitive areas of the patient's bone. This improves the efficiency, safety and reliability of the surgical procedure, particularly in cases where the depth of the drill must be carefully monitored and guided, in order to prevent injury to vulnerable areas in the bone, such as nerves or blood vessels that lie on the drill's path.

The present invention measures the location of the bottom of the drill relative to the surrounding bone by means of ultrasound (US) radiation and makes that information immediately available to the surgeon. The ultrasound is transmitted and received via the jet of liquid running from the drill.

US transmission through a liquid jet was described as a confirmation sensor of a drill in its position in a drilling machine (U.S. Pat. No. 5,850,184), as a dental tool for removing plaque from teeth and for cleaning teeth (U.S. Pat. No. 5,013,241), a high velocity pulsating jet stream for the removal of the dental plaque (U.S. Pat. No. 4,012,842), A thermal imaging system for detecting cracks in tooth, by applying an US dental cleaning tool that transmits US energy through a jet of water to the tooth. This causes cracks in the tooth to heat up and a thermal camera is used to detect the thermal radiation emitted by the heated cracks (U.S. Pat. No. 6,437,334B1).

Another possibility is to sweep angularly with the jet of water that carries the US, and by this one is able to obtain an image of a section or of a volume.

US radiation is a proven technology used in many medical diagnostic applications and was also applied for bone diagnostics—density, structure and velocity of propagation (U.S. Pat. No. 6,030,221, U.S. Pat. No. 5,006,984, U.S. Pat. No. 5,115,813, U.S. Pat. No. 5,402,781, U.S. Pat. No. 5,518,008, U.S. Pat. No. 5,564,423, U.S. Pat. No. 5,651,363). These parameters are important in order to investigate the correct value of the distance mentioned earlier. The radiation levels applied during the use of the present invention are in an accepted range for diagnosis and therefore pose no harm to the patient or the surgeon. Temperature gradients of the radiated area are negligible, especially when the US radiation is transmitted via a liquid jet as in the case of the present invention.

The present invention is particularly advantageous for surgery where depth measurements in the mandible and the maxilla are required, as for example, in mandible intra-osseous implantations.

Another advantage of the present invention for such surgery is that the US radiation is applied through an existing jet of liquid (usually distilled water) flowing from the dental tool. Therefore no additional medium is required, keeping the dimensions of the drill fitted with present invention small and well suited for work within restricted volumes, like the mouth.

The present invention provides the surgeon with real-time information; is relatively inexpensive compared to other, less satisfactory imaging alternatives; and saves time for both the patient and the surgeon (since there is no need to move imaging equipment in and out or to interrupt the surgical procedure).

In summary, it is a main object of the present invention to provide a probe for use in dental surgery for measuring distance from a bottom of a drill to surrounding bone, the probe provided with a mechanism for transmitting and receiving ultrasonic signals, a mechanism for processing the ultrasonic signals to determine the distance to the tissue, and a mechanism for communicating that information to the surgeon.

BRIEF DESCRIPTION OF THE INVENTION

There is thus provided in accordance with a preferred embodiment of the present invention, a device for determining the internal structure of a bone along a path directed into the bone, the device comprising:

a nozzle fluidically connected to a liquid reservoir for providing a liquid jet directed at the bone in the direction of the path;

an ultrasonic transducer for generating ultrasonic waves through the liquid jet and for detecting echoes of the ultrasonic waves caused by changes in the acoustical impedance in the bone characterizing changes in the structure of the bone along the path;

an analyzer for interpreting the echoes into meaningful information relating to the location of the structural changes along the path.

Furthermore, in accordance with some preferred embodiments of the present invention, the device is incorporated in a surgery tool.

Furthermore, in accordance with some preferred embodiments of the present invention, the surgery tool is a drill.

Furthermore, in accordance with some preferred embodiments of the present invention, the drill is hollow, allowing the liquid jet to pass through the drill.

Furthermore, in accordance with some preferred embodiments of the present invention, the liquid jet is outside the drill, directed to a tip of the drill.

Furthermore, in accordance with some preferred embodiments of the present invention, there is provided a method for determining the internal structure of a bone along a path directed into the bone, the method comprising:

providing a liquid jet directed at the bone in the direction of the path;

generating ultrasonic waves through the liquid jet and detecting echoes of the ultrasonic waves caused by changes in the acoustical impedance in the bone characterizing changes in the structure of the bone along the path; and interpreting the echoes into meaningful information relating to the location of the structural changes along the path.

Furthermore, in accordance with some preferred embodiments of the present invention, the method is incorporated in surgery.

Furthermore, in accordance with some preferred embodiments of the present invention, the surgery involves drilling into the bone.

Furthermore, in accordance with some preferred embodiments of the present invention, the method is implemented simultaneously with the drilling.

Furthermore, in accordance with some preferred embodiments of the present invention, the method is implemented when drilling is halted.

BRIEF DESCRIPTION OF THE FIGURES

The invention is described herein, by way of example only, with reference to the accompanying Figures, in which like components are designated by like reference numerals.

FIG. 3B depicts a tip of a drill similar to the one shown in FIG. 3A. However in this example, the drill itself is hollow, allowing a liquid jet to pass through.

DETAILED DESCRIPTION OF THE INVENTION

The present invention is based on transmitting ultrasonic (US) waves through a guided jet of liquid, such as distilled water, targeted to a bone or other tissue or a combination thereof (hereinafter—bone), in order to determine the internal structure along a path in the direction of the impinging jet. The echoes of the US waves are used to determine changes in the acoustical impedance of the bone characterizing changes in the internal structure, and determine their location along that path.

In one preferred embodiment, according to the present invention, the device is incorporated in a drill or other penetrating medical device, so as to provide the surgeon with information on the path along which the tool is penetrating the bone, and specifically distances to structural changes in the bone, thereby preventing or greatly reducing the risk of inflicting damage to vulnerable tissue.

However, the present invention is not limited to such incorporation, and a basic device, in accordance with some preferred embodiments of the present invention, would include only the provision of US transducer for provision of US waves carried by a liquid jet towards the surface of the bone, and for detecting echoes reflected from structural changes within the bone along a path in front of the impinging jet.

The measurement provided by the present invention is based on US wave propagation through a material. When there is a change in the velocity of propagation (i.e. a change in the acoustic impedance), reflections are obtained. These echoes are detected and provide finally electronic signals, which are finally interpreted as distances (given the velocity of propagation through the examined medium is known from these US measurements) where the reflections appeared.

It is known that the velocity of propagation of US waves through the bone varies. It is different for the upper and lower jaws. It is also different between males and females. It may vary with age. It also varies in different locations within the bone. In order to overcome this and take it into consideration in the measurement several methods may be incorporated. These include, for example, measuring the time intervals between the transmitted pulses and the received echoes, and at the same time measuring the velocity of propagation in the bone.

Accordingly, in order to properly conduct a distance measurement, it is important to measure simultaneously both the time between the transmitted and received waves as well as the velocity of propagation at the desired depth.

The US waves are transmitted through the jet of liquid, which is directed toward the bottom part of the bore produced by the drill, and into the bone under the bottom of the bore. Abrupt changes in the acoustic properties of the matter traversed by the US waves produce US echoes (reflections).

Figure 1:
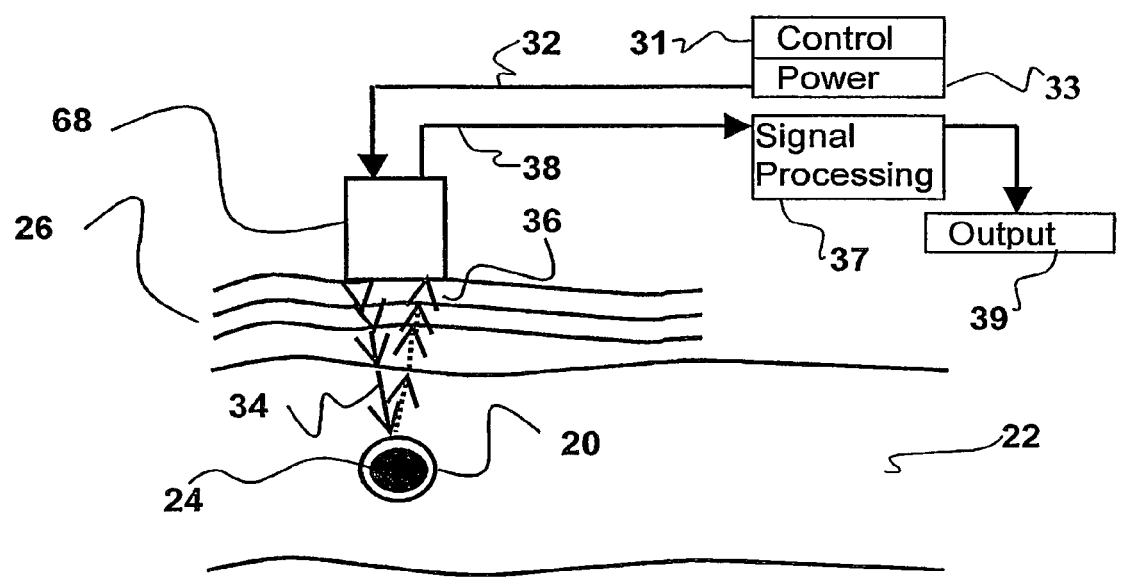
FIG. 1 illustrates how US waves are transmitted through, and reflected from, soft and hard layers of the body in accordance with a preferred embodiment of the present invention.

FIG. 1 illustrates in principle how this property of US waves is put to use in the present invention. Power signals 32 are sent from power 33 circuits to US transducer 68. The control electronics 31 controls the power circuits 33. In the following case, US transducer 68 transmits US waves 34 through soft layers 26 and through a bone 22. US waves 34 encounter nerve canal 20 (containing nerve 24), which generates a distinct (mirror like) reflection 36. When reflection 36 returns from canal 20 via bone 22 and soft layers 26, a similar (attenuated) reflection is obtained, but with an opposite polarity. Reflection 36 is received by US transducer 68, which passes data signals 38 back to signal processing unit 37, which calculates (by means of a software) the distance to the cause of the reflection and presents the results to the surgeon, typically as text or graphic output 39.

In a preferred embodiment of the present invention it is possible to preprogram the US examination of the patient with a typical US wave duration of 1 μsec or less, comprising sinusoidal waveforms that are typically in a frequency range of 10 to 20 MHz and with every wave lasting a fraction of a period to several periods. These are sample specifications and they can vary according to the application. They are presented here for illustrative purposes and do not limit the scope of the present invention.

Figure 2A:
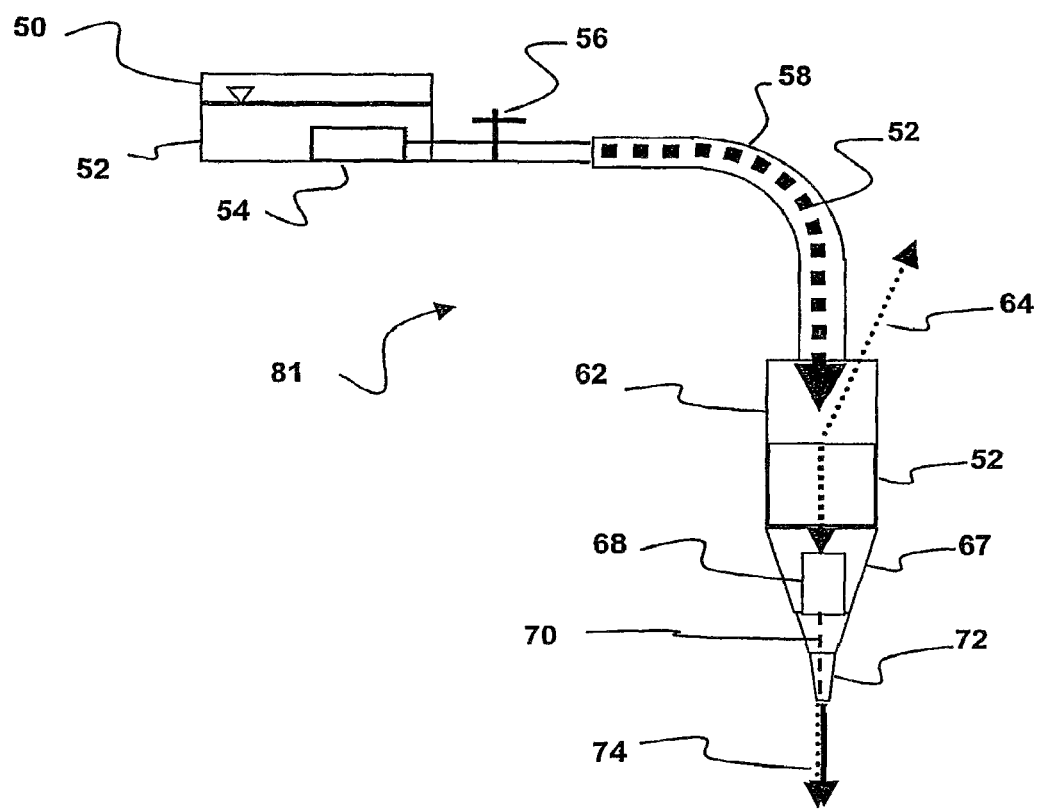
FIG. 2A illustrates a US transducer integrated into a liquid jet in an interactive ultrasound-based depth measurement device in accordance with a preferred embodiment of the present invention.

FIG. 2a illustrates a US transducer integrated into a liquid jet in a interactive ultrasound-based depth measurement device 81 in accordance with a preferred embodiment of the present invention. US transducer 68 is located in vessel 67 through which liquid 52 (usually distilled water) flows. Liquid 52 starts in main reservoir 50 and is pumped by pump 54, when tap 56 is open, through pipe 58 to front reservoir 62. Liquid output from front reservoir 62 passes out of funnel and tube 72 (typically with a diameter in the range of 1 mm to 2.5 mm) and flows against the adjacent tissue or directly on the bone. The pump is preferably a pump that delivers constant mass flow rate, due to medical considerations, but this is not a requirement of the ultrasonic measuring system, hence the present invention is not limited to such pump. An example of such pump is OsseoCare™ Drilling Equipment from Nobel BioCare AB, Sweden and which also includes a torque limiter in order to avoid the mechanical overloading of the bone tissue. US transducer 68 is connected electrically 64 to electronic circuitry, such as a control unit, a power unit, a signal processing unit, an output unit, and sub-units of the transducer. US transmit and receive signals 70 from/to US transducer 68 follow the path 74 of liquid 52.

It should be noted that what is germane to the present invention is that the US transducer be located such that the wave that it transmits and reflection that it receives pass through the liquid jet, such that the jet provides the medium between the transducer and adjacent tissue or bone. Several mechanisms for providing a liquid jet are known. Which specific mechanism is used to generate the liquid jet for the present invention can vary and is not essential to the invention as long as the transducer of the present invention is situated such that it transmits and receives via the jet to the adjacent tissue or bone. In a preferred embodiment of the present invention, the liquid jet is adapted to serve both for the regular operation of a dental drill (cooling the bone and the drill and cleaning the bore from the drilled materials) and for operation of the interactive ultrasound-based depth measurement of the present invention.

Figure 2B:
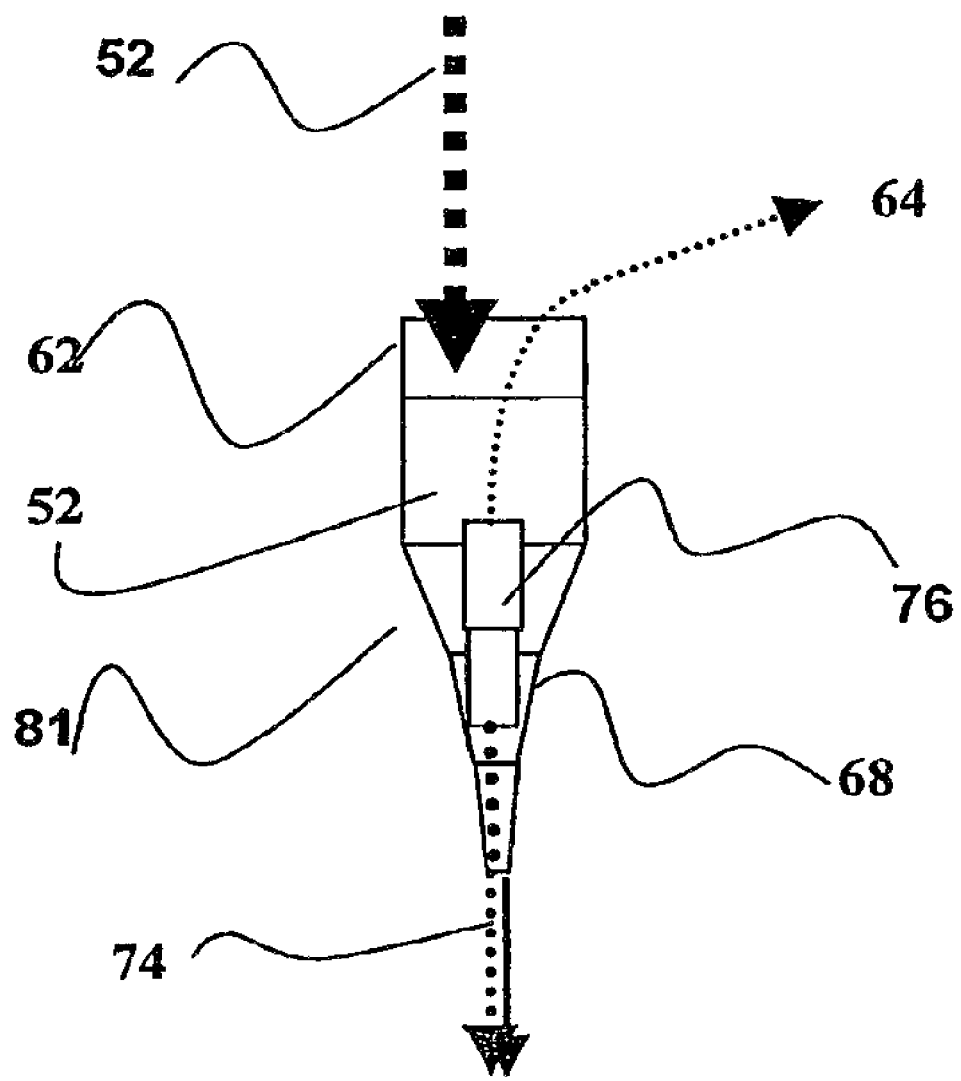
FIG. 2B illustrates front-end electronics located close to the US transducer in order to reduce signal loss in an interactive ultrasound-based depth measurement device in accordance with a preferred embodiment of the present invention.
Figure 3A:
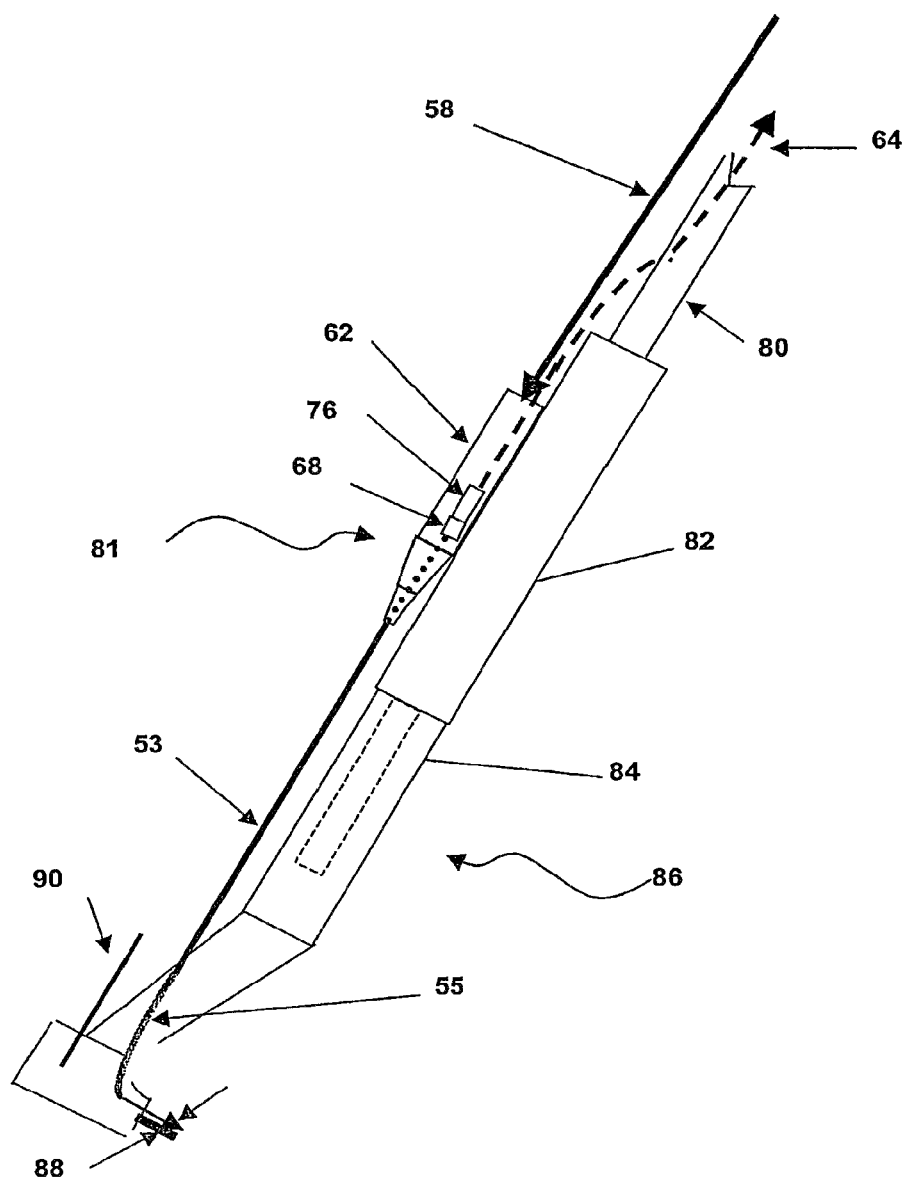
FIG. 3A illustrates an interactive ultrasound-based depth measurement device integrated with a surgical dental drill in accordance with a preferred embodiment of the present invention.

FIG. 2b illustrates an interactive ultrasound-based depth measurement device 81 in accordance with another preferred embodiment of the present invention, wherein front-end electronics 76 are located close to US transducer 68 in order to reduce signal loss and therefore increase the signal-to-noise ratio (S/N). Front-end electronics 76 contains parts of the electronic circuitry, such as a pre-amplifier and parts of the signal processing unit. FIG. 3a illustrates an interactive ultrasound-based depth measurement device 81 integrated with a surgical dental drill 84 in accordance with a preferred embodiment of the present invention. Drill 84 is a standard dental drill, typically comprising power cable 80, which supplies voltage to the electrical motor 82, which turns shaft 84, which is geared to turn drill bit 88 (which is locked in place with drill lock 90). The jet is directed along side the drill 88, aimed at the tip of the drill, or a target just in front of the tip, having a certain angle defined between the jet and the drill.

Figure 3B:
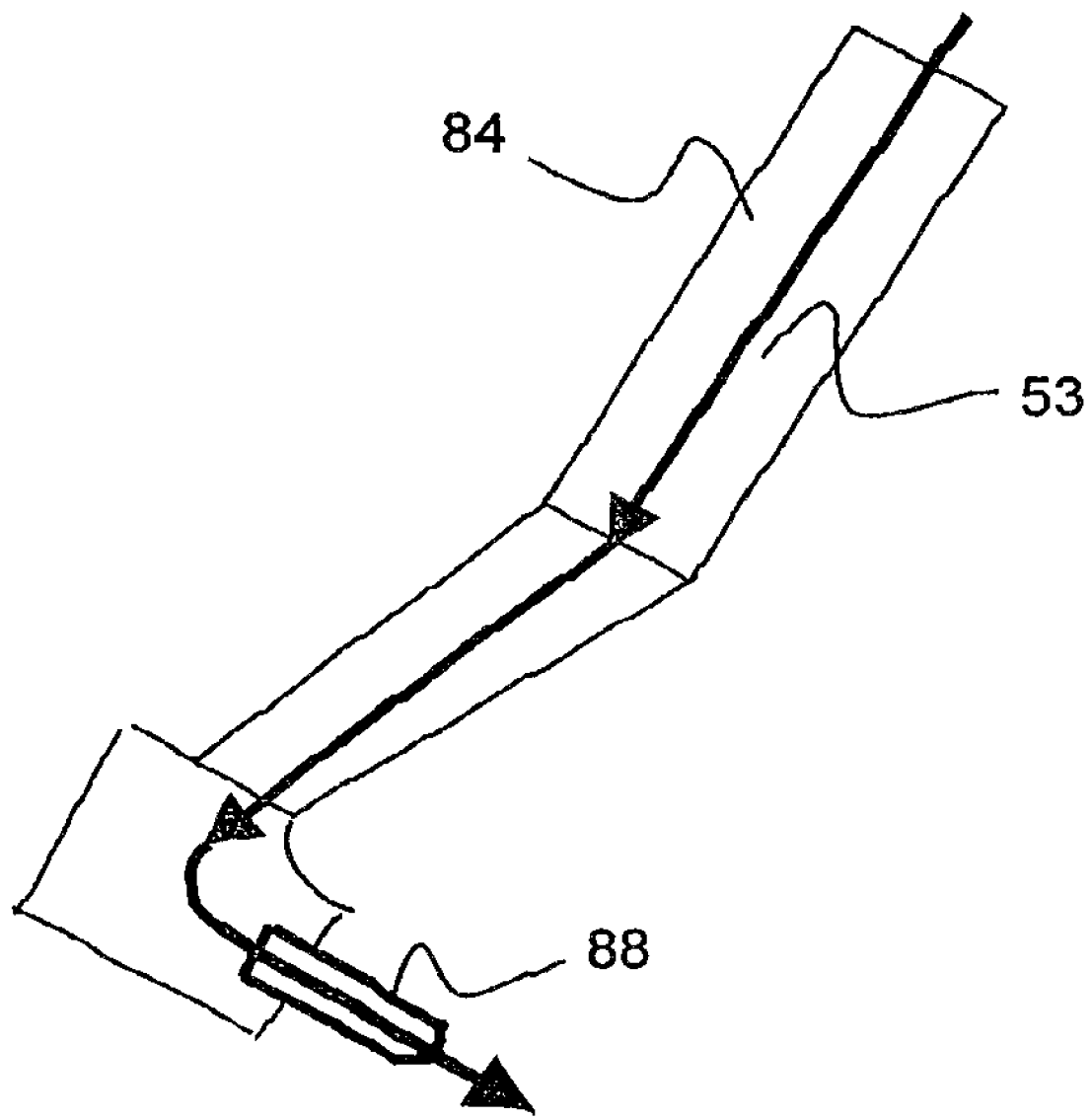

FIG. 3b depicts a tip of a dental drill similar to the one shown in FIG. 3a, but the liquid jet in this tip passes through the drill, via a duct provided along the drill.

The actual distance measurement using the device of the present invention may be carried out while the drill is in use (such as in the case of the embodiment shown in FIG. 3b, where the jet passes through the drill), or when the drill is inactivated, or even retracted from the bore that was drilled, while at the same time directing the jet into that bore. When the jet is along side the drill, and defining a small angle with the drill, it may be practical to withdraw the drill from the drilled bore and direct the jet substantially perpendicular to the bottom of the bore for best results.

Interactive ultrasound-based depth measurement device comprises the components described earlier in this specification with several components adapted for integration with drill 84. These include: additional section of flexible pipe 53 running from funnel and tube 72 to metal tube 55, which exits drill 84 at a point next to drill bit 88, thereby creating egress next to drill bit 88 for liquid carrying transmitted US waves. The liquid serves both its normal function of cleaning and cooling the bore of the drill and its new function (as provided by the present invention) of acting as a medium for transmission of the US waves.

(In the embodiment shown in FIG. 3a or the one shown in FIG. 3b, front-end electronics 76 are installed to reduce signal loss (and therefore increases the S/N), as in FIG. 2B. Alternatively, all depth measurement device 81 electronics can be implemented at the back end, connected to US transducer via electrical connection 64.)

With reference to FIG. 1 and to FIGS. 3a and 3b, during the drilling process, control unit 31 triggers (automatically or manually) transmission of US waves 34 by transducer 68. US wave reflections received back from different density tissues by transducer 68 are passed via link 64 to processing unit 37, which calculates the distance from the bottom of the drilled bore in the mandible to the upper part of the canal 20 (that has a mirror-like reflection) and which contains the nerve and outputs the results to output unit 39 where the surgeon can view them. Typically this output is provided to the surgeon displayed on an alphanumeric or graphical display.

Figure 4:
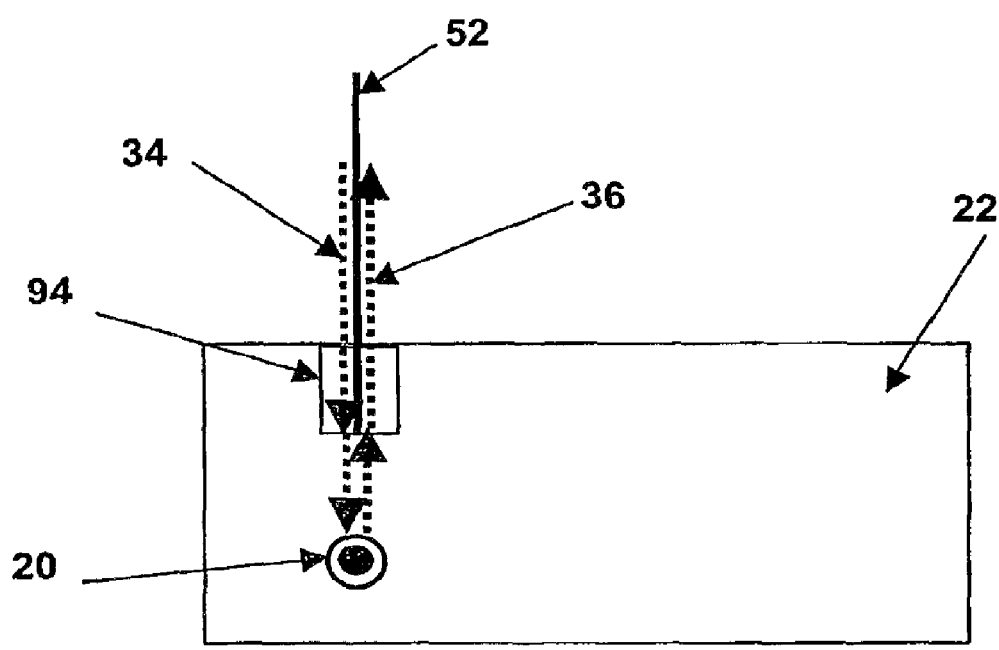
FIG. 4 illustrates how US waves propagate through the jet of liquid in a dental drill integrated with an interactive ultrasound-based depth measurement device in accordance with a preferred embodiment of the present invention.

FIG. 4 illustrates how US waves propagate through the jet of liquid in a dental drill integrated with an interactive ultrasound-based depth measurement device in accordance with a preferred embodiment of the present invention. Jet of liquid 52 flowing into bore 94 in bone 22 serves as medium for transmission 34 of US waves into bone 22 and reception of US reflections 36 from nerve canal 20.

In the case of the mandible, the depth is measured in real time between the bottom of bore 94 and the upper part of nerve canal 20. The depth measurement results are preferably displayed as alphanumeric information, providing the surgeon with an accurate indication of the distance (depth) between the lower part of drilled bore 94 and the upper edge of the sensitive tissue, such as nerve canal 20, that must be avoided with the drill. Alternative displays are also possible (for example graphic representation of the distance).

Figure 5:
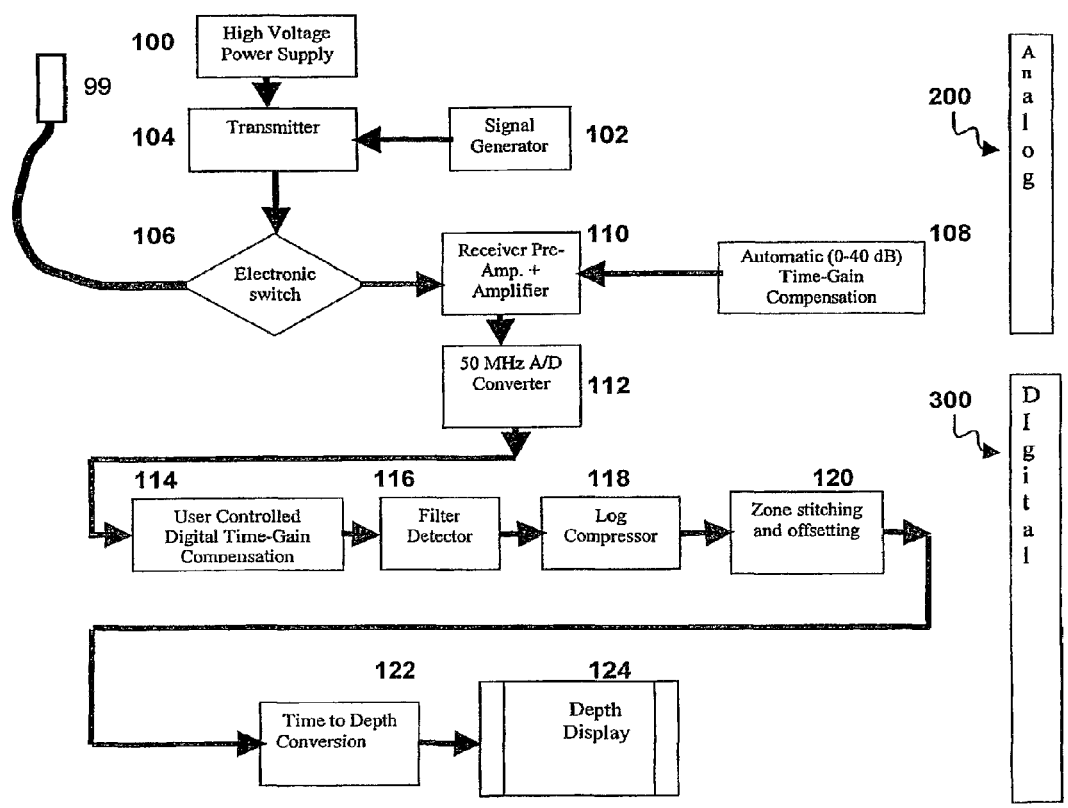
FIG. 5 illustrates a detailed block diagram of analog and digital circuitry for a dental drill with an interactive ultrasound-based depth measurement device in accordance with a preferred embodiment of the present invention.

FIG. 5 illustrates a detailed block diagram of a circuitry for a dental drill with an interactive ultrasound-based depth measurement device in accordance with a preferred embodiment of the present invention. This block diagram operates in an analog 200 mode, and others—which operate in a digital 300 mode. These circuits provide improved noise filtering and signal amplification of transmission of US waves and reception of US wave reflections. The timing of the amplified signals is measured, and assuming known propagation velocity of the ultrasound pulses through bone, the distance from the bottom of the drill bore to the nerve canal is measured and displayed, as described above.

Power is supplied from power supply 100 to transmitter 104, which receives signal from signal generator 102. Transmitter 104 transmits US wave and activates the electronic switch 106, which activates receiver preamplifier and amplifier 110, which receives reflection of wave from different density tissue and time-gain compensation 108. Analog signal is converted 112 to digital and after time-gain compensation 114 is filtered 116, compressed 118, and stitched and offset 120. Calculated time of reflection return is converted to depth measurement 122 and the result is output to display 124.

In a preferred embodiment of the present invention, depth measurement using the present invention can be performed in real time while the drilling is in process or in steps: drilling for a short distance (depth), typically 1 mm to 2 mm and then measuring the distance between the bottom of the drilled bore and the upper edge of the nerve canal before proceeding.

In another preferred embodiment of the present invention, the measurement method can be applied for side measurements (for example, through the gums). One use of this application is identifying the three-dimensional location of the nerve canal (rather than just the linear direction to it).

In another preferred embodiment of the present invention, depth measurement can be applied for other medical applications involving drilling, such as bone implantation, to avoid drilling injury to nerves or blood vessels beneath the drill.

In another preferred embodiment of the present invention, depth measurement can be applied for veterinary medical applications.

In another preferred embodiment of the present invention, it is possible to store the above-mentioned depth measurement on magnetic or other media—for further analysis, comparison, and documentation.

In another preferred embodiment of the present invention, it is possible to incorporate software to control the data transmission to the signal-processing unit and to enable configuring parameters of the invention, for example, to customize the device for pediatric patients. It should be clear that the description of the embodiments and attached Figures set forth in this specification serves only for a better understanding of the invention, without limiting its scope as covered by the following Claims.

It should also be clear that a person skilled in the art, after reading the present specification could make adjustments or amendments to the attached Figures and above described embodiments that would still be covered by the following Claims.

What is claimed is:

1. A device for determining an internal structure of a bone along a drilling path directed into the bone, the drilling path having an axis, the device comprising:
    a nozzle fluidically connected to a liquid reservoir for providing a liquid jet directed at the bone along the axis of the drilling path;
    an ultrasonic transducer aligned with the nozzle along the axis of the drilling path for generating ultrasonic waves through the liquid jet, wherein both said ultrasonic waves are emitted from said transducer and the liquid jet flows from the nozzle along the same axis of the drilling path, said transducer detecting received echoes of the ultrasonic waves traversing back through the jet to the transducer indicative of changes in a tissue along the ultrasonic propagation path, thereby causing an acoustical impedance in the bone characterizing changes in the structure of the bone along the drilling path; and
    an analyzer for interpreting the received echoes into meaningful information relating to the location of the structural changes along the path.

2. The device of claim 1, wherein said analyzer interprets the received echoes into a depth measurement of the drilling path.

3. The device of claim 1, wherein said analyzer interprets the received echoes to determine a distance to a change in the structure of the bone along the drilling path.

4. The device of claim 1, wherein said analyzer is close to said ultrasonic transducer to reduce signal loss and to increase signal to noise ratio.

5. The device of claim 1, wherein said liquid reservoir further comprises a main reservoir for storing said liquid, a front reservoir for receiving said liquid from said main reservoir and a vessel for receiving said liquid from said main reservoir, said vessel being fluidically connected to said nozzle; and a pump for pumping said liquid from said main reservoir to said front reservoir.

6. The device of claim 5, wherein said ultrasound transducer is located within said vessel.

7. The device of claim 1, further comprising a display for displaying said meaningful information.

8. The device of claim 1, wherein said analyzer further comprises a receiver preamplifier and amplifier.

9. The device of claim 8, wherein said analyzer further comprises an analog to digital converter for converting said received echoes to a digital signal; a time gain compensator for compensating for gained time; and a calculator for calculating time of reflection return for calculating a distance to the location of a structural change along the path.

10. The device of claim 9, further comprising software for customizing one or more parameters of operation of said analyzer.

11. A device for determining an internal structure of a bone along a drilling path directed into the bone, the path having an axis, the device comprising:
    a nozzle fluidically connected to a liquid reservoir for providing a liquid jet directed at the bone along the axis of the drilling path;
    an ultrasonic transducer aligned with the nozzle along the axis of the drilling path for generating ultrasonic waves through the liquid jet, wherein both said ultrasonic waves are emitted from said transducer and the liquid jet flows from the nozzle along the same axis of the drilling path, said transducer detecting received echoes of the ultrasonic waves traversing back through the jet to the transducer indicative of changes in an acoustical impedance in the bone characterizing changes in the structure of the bone along the drilling path; and
    an analyzer for interpreting the received echoes into meaningful information relating to the location of the structural changes along the drilling path.

12. A device for determining an internal structure of a bone along a drilling path directed through a soft tissue into the bone, the path having an axis, the device comprising:
    a nozzle fluidically connected to a liquid reservoir for providing a liquid jet directed at the bone along the axis of the drilling path;
    an ultrasonic transducer aligned with the nozzle along the axis of the drilling path for generating ultrasonic waves through the liquid jet, wherein both said ultrasonic waves are emitted from said transducer and the liquid jet flows from the nozzle along the same axis of the drilling path, said transducer detecting received echoes of the ultrasonic waves traversing back through the jet to the transducer indicative of changes in an acoustical impedance in the bone characterizing changes in the structure of the bone along the drilling path; and an analyzer for interpreting the received echoes into meaningful information relating to a distance to the bone along the drilling path.

13. A system for determining an internal structure of a bone along a drilling path directed into the bone, the drilling path having an axis, the system comprising:
- a drill, said drill having a drill tip; and
- a separate device comprising:
  - a nozzle fluidically connected to a liquid reservoir for providing a liquid jet directed at the bone along the axis of the drilling path;
  - an ultrasonic transducer aligned with the nozzle along the axis of the drilling path for generating ultrasonic waves through the liquid jet, wherein both said ultrasonic waves are emitted from said transducer and the liquid jet flows from the nozzle along the same axis of the drilling path, said transducer detecting received echoes of the ultrasonic waves traversing back through the jet to the transducer indicative of changes in an acoustical impedance in the bone characterizing changes in the structure of the bone along the drilling path; and
  - an analyzer for interpreting the received echoes into meaningful information relating to the location of the structural changes along the drilling path; wherein said device is separate from said drill.

14. A method for avoiding an injury to tissue during drilling by a drill along a drilling path directed into the tissue, the path having an axis, the drill having a tip, the tissue comprising bone, the method comprising: providing a device that includes a nozzle fluidically connected to a liquid reservoir for providing a liquid jet, an ultrasonic transducer aligned with the nozzle along the axis of the path for generating ultrasonic waves through the liquid jet, and an analyzer;
- directing a liquid jet at the tissue along the axis of the drilling path;
- generating ultrasonic waves through the liquid jet along the axis of the drilling path by the transducer and detecting received echoes of the ultrasonic waves traversing back through the jet to the transducer indicative of changes in an acoustical impedance in the bone characterizing changes in the structure of the bone along the drilling path, wherein both said ultrasonic waves are emitted from said transducer and the liquid jet flows from the nozzle along the same axis of the drilling path;
- interpreting the received echoes into a meaningful information relating to the location of the structural changes along the drilling path by the analyzer; and
- issuing a warning if the drill tip is damaging or is about to damage the tissue.

15. The method of claim 14, wherein the tissue comprises a nerve, a blood vessel or another soft tissue, or a combination thereof and wherein said structural changes indicate a presence of said nerve, said soft tissue or said blood vessel in said path.

16. A method for determining three dimensional structure of a bone along an axis of a drilling path, the bone being covered at least partially by gum tissue, the method comprising providing a device that includes a nozzle fluidically connected to a liquid reservoir for providing a liquid jet, an ultrasonic transducer aligned with the nozzle along the axis of the path for generating ultrasonic waves through the liquid jet, and an analyzer;
- directing a liquid jet at the gum tissue along the axis of the drilling path;
- generating ultrasonic waves through the liquid jet along the axis of the path by the transducer and detecting received echoes of the ultrasonic waves traversing back through the jet to the transducer indicative of changes in an acoustical impedance in the bone characterizing changes in the structure of the bone along the path, wherein both said ultrasonic waves are emitted from said transducer and the liquid jet flows from the nozzle along the same axis of the drilling path; and interpreting the received echoes into meaningful information relating to the location of the structural changes along the drilling path by the analyzer, thereby providing information regarding the three dimensional structure of the bone.

* * * * *